United States Patent [19]

Carre

[11] Patent Number: 4,758,226
[45] Date of Patent: Jul. 19, 1988

[54] DEVICE FOR DISTRIBUTION, PARTICULARLY FOR MEDICAL USE, OF A PRODUCT IN PREDETERMINED METERED AMOUNTS

[76] Inventor: Maurice Carre, 47, rue Alfred de Musset, Chemin Vert - 1400 Caen, France

[21] Appl. No.: 40,004

[22] Filed: Apr. 20, 1987

[30] Foreign Application Priority Data

Apr. 18, 1986 [FR] France ............................. 86 05611
Apr. 18, 1986 [FR] France ............................. 86 05612

[51] Int. Cl.⁴ .............................................. A61M 5/18
[52] U.S. Cl. ...................................... 604/141; 604/65; 604/247; 604/207; 222/55; 222/14; 310/331
[58] Field of Search ................. 604/67, 140, 141, 143, 604/147, 187, 207, 212, 215, 218, 232, 236, 245–247, 118, 121, 184, 223; 200/81 R, 83 Q, 83 W; 310/311, 314, 317, 331, 340; 128/DIG. 12; 222/14, 55

[56] References Cited

U.S. PATENT DOCUMENTS

| | | | |
|---|---|---|---|
| 817,054 | 4/1906 | Gay | 604/141 |
| 2,001,207 | 5/1935 | McManamna et al. | 604/140 |
| 2,928,409 | 3/1960 | Johnson et al. | 310/317 |
| 3,152,612 | 10/1964 | Avery | 137/625.4 |
| 3,353,537 | 11/1967 | Knox et al. | 604/143 |
| 4,340,083 | 7/1982 | Cummins | 137/499 |
| 4,345,595 | 8/1982 | Whitney et al. | 604/31 |
| 4,354,622 | 10/1982 | Wood | 222/55 |
| 4,392,366 | 7/1983 | Godfrey | 222/55 |
| 4,450,375 | 5/1984 | Siegal | 310/331 |
| 4,542,740 | 9/1985 | Kleinschmidt et al. | 222/55 |
| 4,593,658 | 6/1986 | Moloney | 310/311 |
| 4,644,212 | 2/1987 | Moritugu et al. | 310/317 |

Primary Examiner—Dalton L. Truluck
Assistant Examiner—Frank Wilkens
Attorney, Agent, or Firm—Browdy and Neimark

[57] ABSTRACT

A device for dispensing a product in predetermined metered amounts. The product is contained in a tank including an output orifice associated with means which continuously control the output of product from the tank. The opening of two adjacent valves, each comprising a calibrated nozzle, is controlled by a piezoelectric crystal. Electronic means are provided to control the deformation of the crystals to control the output of product from the tank in predetermined metered amounts.

10 Claims, 3 Drawing Sheets

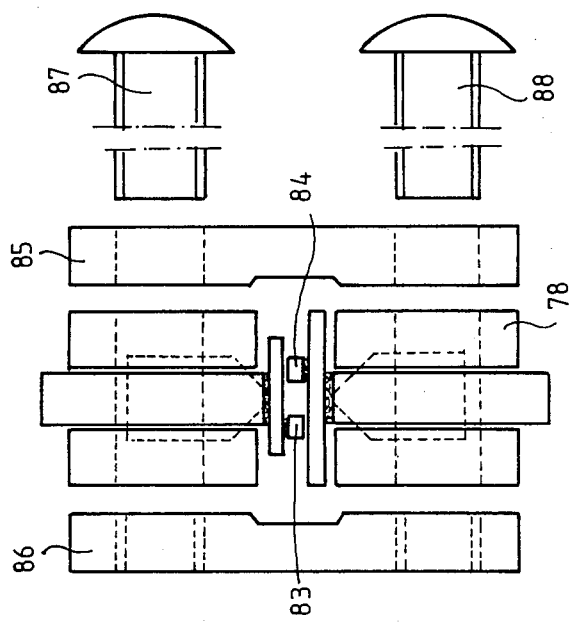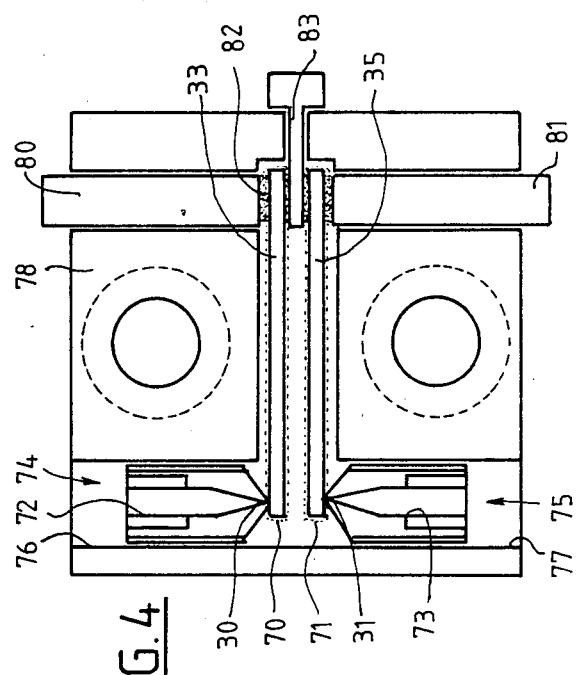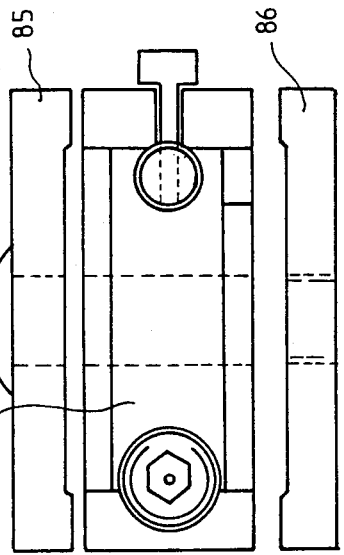

DEVICE FOR DISTRIBUTION, PARTICULARLY FOR MEDICAL USE, OF A PRODUCT IN PREDETERMINED METERED AMOUNTS

FIELD OF THE INVENTION

The present invention relates to a device for distributing a product in predetermined metered amounts.

More generally, the present invention provides a device for distributing a product in liquid or gaseous form in predetermined metered amounts, which device is highly reliable and, therefore can be incorporated in precision metering apparatus, particular in apparatus for medical use.

The present invention in particular, provides a device which can be used to deliver a pharmaceutical product for human or veterinary use in predetermined exact amounts, for treatment or diagnosis, particularly by parenteral injection.

BACKGROUND OF THE INVENTION

It is known that treatment of some diseases requires frequent injections of medicine, for example, daily injections of insulin in the case of certain forms of diabetes. The patients who suffer from such diseases must resort to the care of physicians, nurses or perform the necessary injections themselves. The use of syringes, even of the discardable type, is a nuisance to the user. Further, the handling and preparation necessary for performing the injections with such syringes further increase the unpleasantnesses inherent in such treatments.

Devices have already been proposed seeking to avoid a part of the drawbacks mentioned above during treatments comprising repeated injections of medical substances or the like. In this regard reference is made to French patent No. 2 348 709 and U.S. Pat. No. 4,345,595.

In both of these documents, an injection needle forms the end of a syringe with a mobile piston, the amplitude of the movement of the piston determining the volume injected. If the volume injected is to be determined with precision, mechanical control means become complex, heavy and expensive so that the device is no longer suitable for use in frequent treatments.

SUMMARY OF THE INVENTION

Consequently, an object of the invention is to provide a device whose use is simpler than that of the devices now known for performing percutaneous or intramuscular injections, and such as defined, for example, in the above-mentioned documents.

It is also an object of the invention to provide such a device whose automatic or semiautomatic function is both simple and reliable as required for apparatus for human and animal medical use.

According to a first aspect of the invention, the product to be distributed is contained in a tank comprising an output orifice and with which are associated means continuously urging the output of the product from the tank. On the output path of the product from said tank are provided two adjacent valves or check valves, each comprising a calibrated nozzle which can be opened and/or closed each according to the condition of a deformable piezoelectric crystal, and electronic means for controlling the deformation of said crystals to limit the output of the product from said tank and thus define a predetermined metered amount.

Because of the presence of the two valves or check valves with piezoelectric control, the device according to the present invention has great reliability in functioning, so that it can be used in fields calling for a very great reliability as required in human medicine, such as for injection of insulin.

In another embodiment, the tank of the product to be distributed is a flexible tank or a piston system having means which urge the output of the product to be distributed from said tank. The means control the deformation of said tank or make the piston move.

In a particularly advantageous embodiment, said means are constituted by the effect of pressure, which varies as a function of temperature, of a gas vapor, such as Freon, selected so that its vapor tension characteristics are compatible with the maximum admissible power of the piezoelectric crystals used. One particularly effective gas for this purpose is Freon 13.

According to another characteristic of the invention, the device is provided with means which can trigger a sound or light alarm signal for preestablished functioning conditions, for example, when a certain minimal level is reached in the tank of the product to be delivered, or in case of failure of the electronic control circuit, or again in case of poor functioning of the means assuring the output of the product to be delivered from the tank which contains it.

In another embodiment, the deformation of a piezoelectric crystal is controlled by the voltage supplied by a dc-dc converter whose one input is connected to a comparator which receives, on the one hand, a reference voltage and, on the other hand, a triggering signal.

In this embodiment, the electronic control means further comprise a first amplifier whose one input is connected to a terminal of a first piezoelectric crystal having its other terminal grounded and whose output is connected to one of the terminals of a capacitor whose charging current is adjustable by a variable resistor for initial calibration.

A second amplifier is provided, whose input is connected to said first piezoelectric crystal and whose output translates the state of said crystal ends, at the dc-dc converter.

To determine the predetermined metered amount which the device delivers, the latter further comprises time base means for counting the number of triggering pulses applied to the comparator.

Advantageously, the piezoelectric crystals are protected from the action of the product to be distributed by a protective covering of a material such as a flexible polymeric resin, said covering at the same time opposing electric leakages able to deteriorate, by electrolysis or in a similar way, the product to be distributed.

A second aspect of the invention, provides devices for injecting liquid for medical use, comprising an injection needle and a tank of the product to be injected operationally connected to said needle, with means placed between said tank and said needle to control the flow of the injected product. Said means consist of a piezoelectric device comprising two adjacent valves or check valves each comprising a calibrated nozzle able to be opened and/or closed, each according to the condition of a deformable piezoelectric crystal and electronic means for controlling the deformation of said crystals to limit the output of the product from said tank and thus define a predetermined metered amount.

The invention envisages embodiments differing from one another by the way they are used, for example, as a portable, device rechargeable after performance of a certain number of injections and/or emptying of the reserve of the product to be injected, or as a device for parenteral injection of medicine subcutaneously or intramuscularly over a relatively long period, as required, for example of certain extended continuous treatments in the case of ambulatory pumps or the like.

BRIEF DESCRIPTION OF THE DRAWINGS

The invention will be better understood from the following description, given by way of example and with reference to the accompanying drawing in which:

FIG. 4 is a partial view, on a larger scale, of a part of the device shown in FIG. 1;

FIG. 5 is a corresponding top view, certain parts having been removed from others for clarity;

FIG. 6 is a side view in which certain parts have also been removed from one another for clarity;

DETAILED DESCRIPTION OF THE INVENTION

Figure 1:
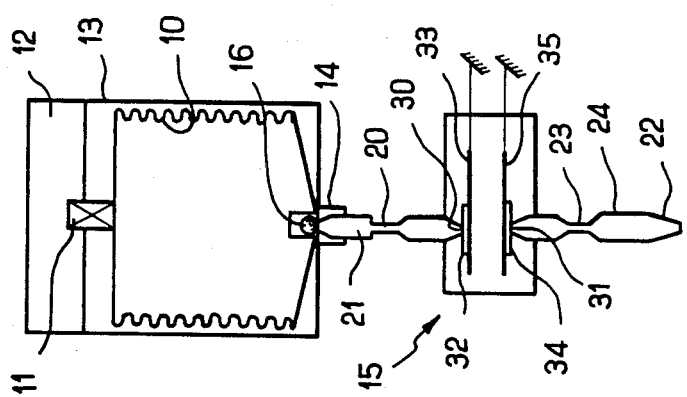
FIG. 1 is a diagrammatic view of a device according to the invention.

A device according to the invention, distributing a product according to the invention in predetermined metered amounts is shown diagrammatically in FIG. 1. The device comprises a tank 10 of product to distributed d which are operationally connected, as diagrammatically shown at 11, means 12 which continuously control the output from said tank of the product contained in the tank.

In the embodiment described and represented, tank 10 is advantageously a deformable flexible tank, contained in an enclosure 13, which also encloses means 12, preferably constituted by reserve of a gas—such as Freon—the vapor pressure of which, at the temperature of using the device, is selected for obtaining a suitable thrust force, causing ejection from tank 10 of the product that it contains by deformation of said tank. Enclosure 13 is also constructed so that it is possible easily to proceed, at will, to replace either gas reserve 12 or the flexible tank of the product to be distributed. The tank is further provided with a means 16, such as a valve or the like with airtight sealing, to allow the initial introduction into reserve 10 of the product to be distributed, but which does not oppose its exit.

In a variation, not shown, the product to be distributed is enclosed in a cylinder and piston system.

With the tank unit as described above, is associated a metering device itself, interposed between tank 10 of the products to be distributed to which it is connected by a capillary 20 and an output tip 22 to which it is connected by another capillary 23. Capillary 20 is interposed on a line 21 for connecting metering device 15 itself and tank 10, while capillary 23 is interposed on a line 24 connecting the output of metering device 15 itself to tip 22.

Device 15 comprises a first calibrated nozzle 30 communicating directly with capillary 20 and a second calibrated nozzle 31 communicating with capillary 23, said nozzles advantageously being made of an injected plastic of the nylon type (registered trademark) or machined stainless steel threaded with a micrometric pitch.

Element 32, carried by a piezoelectric crystal 33, works with the output orifice of nozzle 30, the prestress of which brings said element 32 in contact with said orifice to assure its closing, while the product to be distributed escapes through said orifice when element 32 is separated by the product under pressure by deforming piezoelectric crystal, thus producing an electric charge at its terminals. Similarly, with the calibrated output orifice of nozzle 31 an element 34, carried by a piezoelectric crystal 35, works whose movement opens or closes the orifice of nozzle 31 airtight, the opening force of the valves which is formed by said nozzle 31 and element 34 being limited by the diameter of capillary 23, which also limits the output flow of the product to be distributed.

Figure 2:
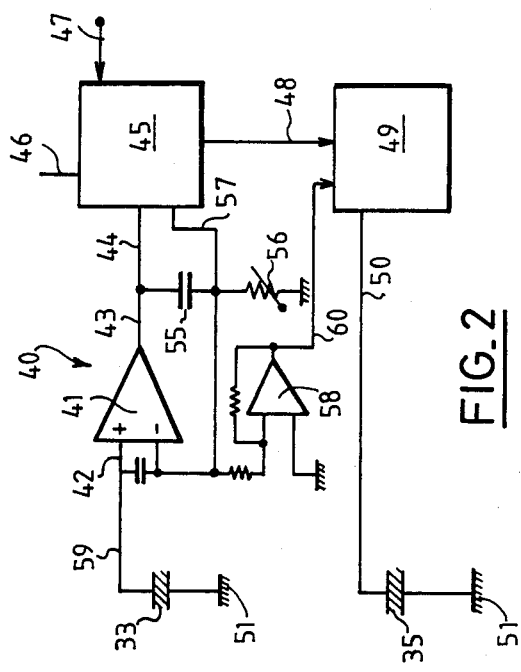
FIG. 2 is a circuit diagram of the device of the present invention.

According to the invention, piezoelectric crystals 33 and 35 are controlled by electronic circuit 40, FIG. 2, which comprises an amplifier 41 whose input 42 is connected to a terminal 59 of crystal 33 and output 43 is connected to an input 44 of a comparator 45 which receives on a terminal 46 a reference voltage and on another input 47 a triggering signal. Output 48 of comparator 49 is connected to a dc-dc converter 49 whose output 50 is connected to a terminal of piezoelectric crystal 35, the other terminal of the latter being connected to ground 51.

A capacitor 55, shunted on output 43 of amplifier 41 is provided with a capacitor whose charging current is adjustable by variable resistor 56, the voltage at terminals of said capacitor 55 being applied to comparator 45 by in input terminal 57.

A second amplifier 58, also connected to terminal 59 of piezoelectric crystal 33, supplies on its output 60—connected to converter 49—an image of the state of said crystal.

Operation of a device according to the invention is the following.

Tank 10 being filled with the product and means 12 being operative, the product to be distributed exits said tank.

Under an initial condition which is that shown diagrammatically in FIG. 1, the output orifice of nozzle 30 is blocked by airtight contact cooperation of element 32 and said orifice, just as the orifice of nozzle 31 is closed by airtight cooperation with that of element 34. No voltage exists at the terminals of piezoelectric crystal 33 nor is applied to the terminal of piezoelectric crystal 35; there is no distribution of the product from tank 10.

If, starting with this condition, a triggering pulse is applied to input terminal 47 of comparator 45, output 48 of the latter flips and causes converter 49 to be put into operation. The voltage then increases at the terminals of piezoelectric crystal 35 and when the voltage at the terminal of said crystal reaches a value V—as shown in the diagram of FIG. 3 in which time is the abscissa and the values of the voltage at the terminal of piezoelectric crystal 35 comprise the ordinate—said crystal deforms effectively and rapidly while the voltage at its terminal decreases to be limited to a value $V_2$ for which a residual deformation exists sufficient to provide for a surface opening equal to the surface of capillary 23, which thus limits the maximum flow of product, on the one hand, and also limits, on the other hand, the opening force of the valve consisting of nozzle 31 and element 34.

Simultaneously with the deformation of piezoelectric crystal 35, which controls the opening of nozzle 31, piezoelectric crystal 33 is also deformed by the passage of the product, which causes the appearance on its terminal 59 of a voltage which, applied by input 42 to amplifier 41, advantageously an amplifier of the very high-impedance MOS FET type, produces a constant current whose intensity, adjustable by a resistor 56, causes the charging of capacitor 55, the voltage which appears on the terminals of the latter then being the indication of the amount of product released.

Figure 3:
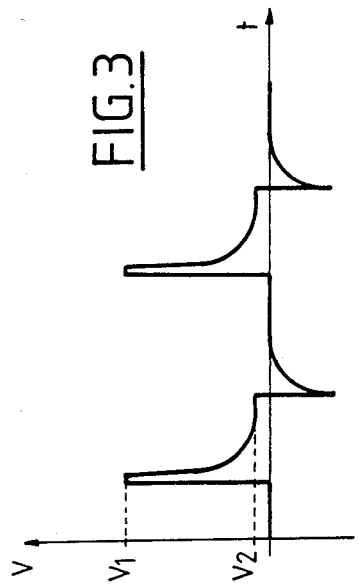
FIG. 3 shows a wave form used in the device according to the present invention.

When this voltage reaches the value of reference voltage applied to input 46 of comparator 45, output 48 of the comparator flips and, the output of converter 49 is reversed or brought back to zero, as shown in the diagram of FIG. 3. The orifice of nozzle 31 is closed by return of crystal 35 to its initial condition and is kept closed by the pressure that is exerted on the piezoelectric crystal which prevents any new output of the product. The simultaneous return of crystal 33 to its initial condition, i.e., that at which element 32 works with the output of calibrated nozzle 30, brings back to zero the voltage at the terminals of the piezoelectric crystal.

During this stage, capacitor 55 is also short-circuited so that the appearance of a new triggering pulse on input 47 controls the course of a cycle identical with that described above and, consequently, the output from tank 10 of a new predetermined metered amount of the product to be distributed.

Then the amount of product dispensed will be determined by adjusting and counting, by means not shown, of the number of triggering pulses on input 47 of comparator 45.

The output of amplifier 58—which is the image of the condition of piezoelectric crystal 33, i.e., the condition of the valve which is formed by element 32 carried by said crystal and calibrated nozzle 30—controls, during the cycle defined above, the passage from high to medium voltage and supplies, outside the periods corresponding to opening of the valves of device 15, an indication on a possible residual flow at right angles with the calibrated orifice of nozzle 30, so that its output can constitute the input signal of an alarm circuit.

Triggering of the latter can advantageously be dependent on a second time base, whose start is synchronous with that of the control of application of triggering pulses on input 47 of comparator 45.

The invention also provides for causing the triggering of an alarm in response to factors such as the absence of product in tank 10, a failure of means 12 tending to cause the ejection of the product, a failure of the electronic circuits and of their power supply.

To protect piezoelectric crystals 33 and 35 from the chemical and physicochemical action of the product dispensed, the invention provides for coating said crystals with a polymeric resin, for example, a flexible epoxy type resin. Such a treatment additionally has the advantage of avoiding any electric leakage able to deteriorate the product to be dispensed, for example, by electrolysis.

As shown in FIGS. 4 to 6, piezoelectric crystal 33 and 35, coated with a resin film 70 and 71, respectively, work with nozzles 30 and 31 made at the ends of longitudinal bores 72 and 73 made in parts 74 and 75 oval in shape screwed and glued in opposite cylindrical bores 76 and 77 of a body 78 of insulating material. In the insulating material are also mounted pushers 80 and 81 which are electrically connected by zones of conductive glue 82 and 83, respectively, to piezoelectric crystal 33 and 35 between which are further interposed spacers 83 and 84, also in electrically conductive relation by a conductive glue, for example a silver glue, with said crystals.

Covers 85 and 86 work with body 78. These covers are fastened to the body by bolts 87 and 88 and are made airtight by seals (not shown).

Figure 7:
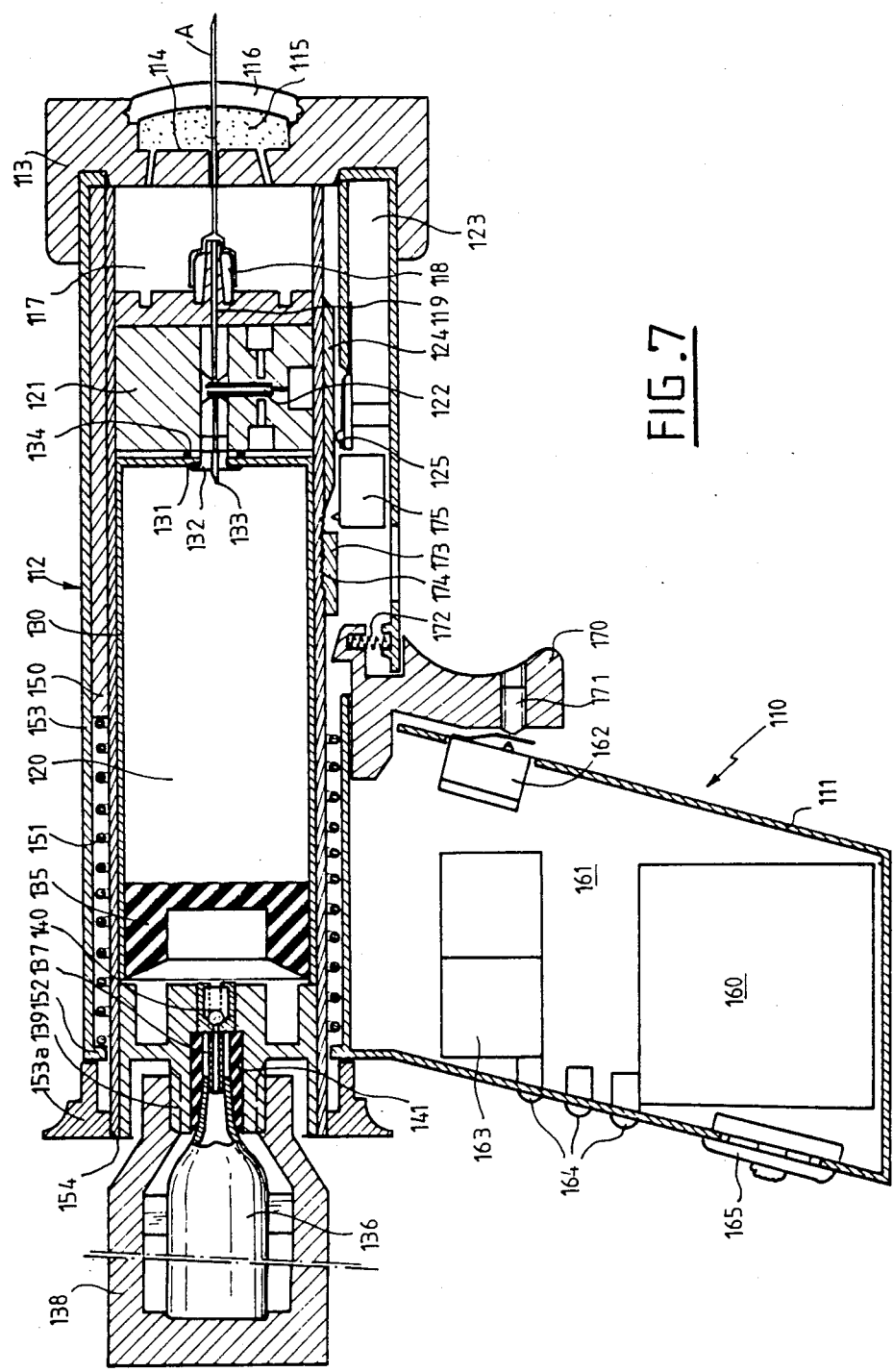
FIG. 7 is a diagrammatic view, in longitudinal section, of a device for injection of liquid for medical use.

For distribution by injection of a liquid in predetermined metered amounts, for example, insulin, a device 110 (FIG. 7) is provided in the form of a pistol with butt 111 and barrel 112 made by assembling two half shells mounted on guide rails. Barrel 112 is blocked by a sterile plug 113 in which is made a housing 114 of a pellet 115 of solid formol or the like kept in place by a hermetic plug 116. Into sterile space 117, which is closed by plug 113, projects an element 118 for connecting an injection needle, not shown, which is pierced by a channel 119 for passage of the product to be injected delivered from a reserve 120 by a micrometering device 121 for checking and control of the flow of the product to be injected and which is of the type of that described above in reference to FIGS. 1 to 6.

This device, which comprises piezoelectric crystals 122, is controlled by electronic means (not shown), placed in a housing 123 of barrel 112, the electric connection of said means to micrometering device 121 being achieved by plates 124, on the one hand, and by contact springs 125, on the other hand.

In a first embodiment, represented in the drawing, reserve 120 of product to be injected is contained in a cylinder 130 whose output orifice is equipped with a silicone rubber sealing means 132, through which passes a needle 133 for striking and taking of the product, an O ring 134 being placed between the outside face of cylinder 130 and the device of micrometering device 121. In cylinder 130 is housed a silicone rubber or similar piston 135 on which is exerted the effect of pressure of a gas contained in a cartridge 136, for example of liquid Freon, means 137 known in the art for striking cartridge 136 being operative when a covering 138 of cartridge 136 is screwed onto a body 139 which also contains a check valve 140 and a rubber sealing ring 141.

In a variant, not shown, the liquid to be injected is contained in a plastic bag housed in body 130.

The unit of injection needle A, metering device and reserve of product to be injected is mounted to slide in slides of barrel 112 of the device by means of three guide rails 150 angularly equidistributed around the axis of the barrel and on which is exerted the action of a spring 151 thrusting at its back end on a stop 152 of body 153 of the barrel and whose position can be adjusted by a knurled ring 153a with inside thread 154 working with the body of the device.

In butt 111 are housed electric power supply batteries 160, electronic control and checking means 161 and a trigger contact 162. A minidigit display device 163 or the like is visible on the butt, as well as light-emitting diodes 164 and a start-stop switch 165.

Trigger 170, which comprises an adjustment screw 171 of microcontact 162, is subjected to the action of a return spring 172. A trigger stop 173, whose position is adjustable by a rack 174, is provided on the body of barrel 112, in the vicinity of an arming microcontact 175 in the unarmed condition of the device.

The device operates as follows: after using switch 165, to begin operation, which causes resetting of electronic means and putting metering device 121 into operation, injection needle A is placed on connection element 118 and the length of exit of said needle is adjusted by action on knurled ring 153a.

By a suitable embodiment of circuits 161 the activation of trigger 170 causes a first activation of microcontact 162 which controls the purge of needle while keeping the electronic system of micrometering device 121 looped on itself and the release of a microdose of product to be injected during release of trigger 170.

The injection device is armed by a backward movement similar to cocking a pistol. This purely mechanical action does not affect the electronic means, with the exception of the light-emitting diodes 164, one of which is lit to indicate that the device is armed. Then, on means 163, the dose to be injected is displayed and again trigger 170 is activated to release trigger stop 173 and to cause the forward movement, under the action of previously compressed spring 151, of the mobile unit comprising the injection needle, the reserve of liquid to be injected and the metering device.

The latter is simultaneously made operative, as described with reference to FIGS. 2 and 3, and, when arming light-emitting diode goes out and injection light-emitting diode goes on, said injection begins and is continued until the dose to be injected has been dispensed.

An alarm device which, among other functions, receives the signals from micrometering device 121 and also takes into account the value of the voltage of batteries 160, makes it possible to stop the injection in case of necessity and/or indicates that the batteries must be replaced.

Another device has been made according to the invention for dispensing insulin by using a flexible tank with deformation controlled by the action of the vapor pressure of a Freon 113, having a value of 8 kg/cm$^2$ at 30° C.

The diameter selected for the capillaries was on the order of 72.5 micrometers, the diameter of the calibrated nozzles was about 1000 micrometers and that of the seats working with said nozzles was about 2000 micrometers.

Piezoelectric crystal 33 was of the PXE5 type, bimorphous, with a dimension of 12×4×0.6 mm, a free length of 10 mm and coated, with an insulation of a flexible polymerized resin, such a crystal being available from the Philips company under reference 43 22 020 04 610.

Piezoelectric crystal 35, of the same material as that of piezoelectric crystal 33, had dimensions of 12×6×0.6 mm and was available from the Philips company under reference 43 22 020 04 650.

For such an element, the value of the threshold voltage is on the order of 98 volts and the value of the opening voltage, for a deflection of 8 micrometers, is on the order of 32 volts.

The foregoing description of the specific embodiments will so fully reveal the general nature of the invention that others can, by applying current knowledge, readily modify and/or adapt for various applications such specific embodiment without departing from the generic concept, and therefore such adaptations and modifications are intended to be comprehended within the meaning and range of equivalents of the disclosed embodiments. It is to be understood that the phraseology or terminology employed herein is of or the purpose of description and not of limitation.

What is claimed is:

1. A device for dispensing metered amounts of a product from a tank, said device comprising:
    an output orifice;
    means associated with said orifice to dispense product from said tank;
    a control valve and a command valve, said valves being located adjacent each other and located in the output path of said product from said tank;
    a first mechanically deformable piezoelectric crystal associated with said control valve, said first mechanically deformable crystal having a first terminal and a second terminal,
    a second electrically deformable piezoelectric crystal associated with said command valve, said second electrically deformable crystal having a first terminal and a second terminal;
    each of said valves comprising a calibrated nozzle which can be opened or closed in response to the condition of the deformable piezoelectric crystal associated with said valves;
    electronic means for measuring and monitoring the deformation of said crystals to control the output of the product from said tank.

2. The device of claim 1 wherein said tank is a flexible tank and the means for dispensing of the product include means which control the deformation of said tank.

3. The device of claim 2 wherein said tank is enclosed in an enclosure and said means for deforming said tank comprise a gas which has a vapor pressure which varies with temperature.

4. The device of claim 1 wherein the deformation of said second piezoelectric crystal is controlled by the voltage suppled by a dc-dc converter;
    an input of said dc-dc converter is connected to a comparator;
    said comparator receives a reference voltage and a triggering signal;
    said electronic control means futher comprise a first amplifier, an input of which is connected to the first terminal of said first piezoelectric crystal;
    said second terminal of said first piezoelelctic crystal is connected to the ground;
    the output of said first amplifier is connected to a terminal of a capacitor; and
    a variable resistor for adjusting the charging current of said capacitor.

5. The device of claim 4 including a second amplifier, an input of which is connected to said first piezoelectric crystal and the output of which, which translates the state of said crystal, ends at the dc-dc converter.

6. The device of claim 4 further including a time base means for counting the number of triggering pulses applied to said comparator.

7. The device of claim 1 including a body of insulating material;
    calibrated parts mounted in said body of insulating material, said parts forming calibrated nozzles;
    said body having means defining a space for receiving said first and second piezoelectric crystals in an assured position;
    pushers housed in said body for positioning said piezoelectric crystals;
    a protective covering over said piezoelectric crystals for preventing electric leakages able to deteriorate the product to be distributed.

8. A liquid injection device comprising:
    an injection needle;

a reserve of product to be injected connected to said needle;

piezoelectric means interposed between said reserve and said needle;

said means comprising a first valve and a second valve, said valves being adjacent each other;

a first deformable piezoelectric crystal and a second deformable piezoelectric crystal;

each of said valves comprising a calibrated nozzle which can be opened or closed in response to the condition of said first or said second piezoelectric crystal;

electronic means for controlling the deformation of said piezoelectric crystals to define a predetermined metered amount of product.

9. The device of claim 8 in the form of a pistol;

a trigger on the pistol to control injection of said product;

a unit comprising an injection needle holder, piezoelectric means, and product reserve;

said trigger controlling said unit;

electronic means for controlling and checking of the flow of product to be injected;

a microcontact for controlling the operation of said trigger.

10. The device of claim 9 wherein said pistol includes a butt portion;

a stop-start switch, means for displaying the state of the device, and means for displaying doses to be injected located on said butt portion.

* * * * *